(12) United States Patent
Larsen et al.

(10) Patent No.: US 11,446,351 B2
(45) Date of Patent: Sep. 20, 2022

(54) COMPOSITION FOR TREATING ONE OR MORE ESTROGEN RELATED DISEASES

(71) Applicant: LIFEARC, London (GB)

(72) Inventors: Finn Larsen, Hawick (GB); Carol Marion Maclean, Bathgate (GB)

(73) Assignee: LIFEARC, London (GB)

( * ) Notice: Subject to any disclaimer, the term of this patent is extended or adjusted under 35 U.S.C. 154(b) by 0 days.

(21) Appl. No.: 17/050,430

(22) PCT Filed: Apr. 25, 2019

(86) PCT No.: PCT/EP2019/060570
§ 371 (c)(1),
(2) Date: Oct. 23, 2020

(87) PCT Pub. No.: WO2019/207026
PCT Pub. Date: Oct. 31, 2019

(65) Prior Publication Data
US 2021/0052692 A1 Feb. 25, 2021

(30) Foreign Application Priority Data
Apr. 26, 2018 (EP) ..................... 18169419

(51) Int. Cl.
*A61P 5/30* (2006.01)
*A61K 38/09* (2006.01)
*A61P 5/32* (2006.01)

(52) U.S. Cl.
CPC ............... *A61K 38/09* (2013.01); *A61P 5/32* (2018.01)

(58) Field of Classification Search
CPC combination set(s) only.
See application file for complete search history.

(56) References Cited

U.S. PATENT DOCUMENTS

| | | | | |
|---|---|---|---|---|
| 5,658,884 | A * | 8/1997 | Hodgen | A61K 38/09 514/10.2 |
| 2002/0177556 | A1 | 11/2002 | Engel et al. | |
| 2003/0044463 | A1 * | 3/2003 | Deghenghi | A61K 38/09 424/468 |
| 2006/0100155 | A1 * | 5/2006 | Riethmuller-Winzen | A61K 45/06 514/10.4 |

FOREIGN PATENT DOCUMENTS

| | | | |
|---|---|---|---|
| WO | WO9520972 | A1 | 8/1995 |
| WO | WO9603138 | A1 | 2/1996 |
| WO | WO0121194 | A2 | 3/2001 |
| WO | WO03006049 | A1 | 1/2003 |
| WO | WO-03022243 | A2 * | 3/2003 ............ A61K 38/09 |

OTHER PUBLICATIONS

Limonta et al., "Gonadotropin-releasing hormone receptors as molecular therapeutic targets in prostate cancer: Current options and emerging strategies," Cancer Treatment Reviews 39 647-663 (2013) (Year: 2013).*
Chen et al., "Discovery of . . . (Elagolix), a Potent and Orally Available Nonpeptide Antagonist of the Human Gonadotropin-Releasing Hormone Receptor," J. Med. Chem. 2008, 51, 7478-7485 (Year: 2008).*
Tafi et al., "Advances in pharmacotherapy for treating endometriosis," Expert Opinion on Pharmacotherapy 16:2465-2483 (2015) (Year: 2015).*
Holford, "A size standard for pharmacokinetics," clinical Pharmacokinetics 30: 329-332 (1996) (Year: 1996).*
Merck Manual Breast Cancer accessed Aug. 21, 2014 at URL: merckmanuals.com/home/womens_health_issues/breast_disorders/breast_cancer.html) (Year: 2014).*
Ovarian Cancer, accessed Aug. 21, 2014 at merckmanuals.com/home/womens_health_issues/cancers_of_the_female_reproductive_system/ovarian_cancer.html?qt=ovarian cancer&alt=sh (Year: 2014).*
Merck Manual Cancer of the Uterus, accessed Aug. 21, 2014 at URL: merckmanuals.com/home/womens_health_issues/cancers_of_the_female_reproductive_system/cancer_of_the_uterus.html?qt=Cancer of the Uterus&alt=sh (Year: 2014).*
Alzheimer's disease, Merck manual Alzheimer's disease, accessed Sep. 11, 2021 at URL: merckmanuals.com/professional/neurologic-disorders/delirium-and-dementia/alzheimer-disease?query=Alzheimer's (Year: 2021).*
Finas et al, "Cetrorelix in the treatment of female infertility and endometriosis," Expert Opin. Pharmacother. 7:2155-2168 (2006) (Year: 2006).*
International Search Report and Written Opinion Appl. No. PCT/EP2019/060570 dated Jul. 10, 2019.
International Preliminary Report on Patentability (IPRP), Appl. No. PCT/EP2019/060570 dated Aug. 7, 2020.
Jacques Donnez et al., "Partial Suppression Of Estradiol: A New Strategy In Endometriosis Management?", Fertility and Sterility®, vol. 107, No. 3 Mar. 2017 pp. 568-570, (Year 2017).

(Continued)

*Primary Examiner* — Julie Ha
*Assistant Examiner* — Kristina M Hellman
(74) *Attorney, Agent, or Firm* — Fox Rothschild LLP

(57) ABSTRACT

The present invention relates to treating one or more estrogen related diseases while preventing or reducing the likelihood of developing estrogen deficiency related side effects, wherein the composition comprises administering a therapeutically effective amount of a Gn RH antagonist to a patient in need of the treatment, and wherein the amount of Gn RH antagonist is sufficient for providing a mean endogenous serum estradiol level of between about 20 pg/ml and 60 pg/ml, preferably between 30 pg/ml and 50 pg/m, in the patient in a treatment period of at least four weeks, without relying on "add-back" therapy. The composition and method are simple, effective and will accordingly both increase patient acceptance and compliance of therapy.

4 Claims, 6 Drawing Sheets

(56) References Cited

OTHER PUBLICATIONS

Olof Stephansson et al., Original Article, Reproductive Epidemiology, "Endometriosis, Assisted Reproduction Technology, And Risk Of Adverse Pregnancy Outcome", Human Reproduction, vol. 24, No. 9 pp. 2341-2347, 2009.

Robert L. Barbieri, MD, "Hormone tTeatment of Endometriosis: The Estrogen Threshold Hypothesis", Am. J. Obstet. Gynecol., vol. 166, No. 2., pp. 740-745 (1992).

Eric S. Surrey, MD et al., "Prolonged Gonadotropin-Releasing Hormone Agonist Treatment Of Symptomatic Endometriosis: The Role Of Cyclic Sodium Etidronate And Low-Dose Norethindrone "Add-Back" Therapy", Fertility And Sterility, vol. 63, No. 4, pp. 747-755, Apr. 1995.

\* cited by examiner

COMPOSITION FOR TREATING ONE OR MORE ESTROGEN RELATED DISEASES

This application is a 371 filing of International Patent Application PCT/EP2019/060570 filed Apr. 25, 2019, which claims the benefit of EP18169419.1 filed Apr. 26, 2018.

TECHNICAL FIELD

The present invention relates to a composition for treating estrogen related diseases, such as endometriosis, while preventing or reducing the likelihood of developing estrogen deficiency related adverse effects.

BACKGROUND

Endometriosis is an estrogen-dependent chronic disease characterized by the growth of hormone-responsive endometrial tissue outside the uterine cavity. Symptoms of endometriosis include, dysmenorrhea, dysparenunia, pain with bowel movements or urination, menorrhagia, menometrorrhagia and infertility.

Endometriosis affect women from menarche to menopause and it is estimated that 30 to 40% of women with endometriosis are infertile. Furthermore, in a cohort study of more than 1.4 million births in Sweden, women with endometriosis were associated with an increased risk of cesarean section, pre-term delivery, preeclampsia and antepartum hemorrhage. (Stephansson O1, Kieler H, Granath F, Falconer H; Endometriosis, assisted reproduction technology, and risk of adverse pregnancy outcome. Hum Reprod. 2009 September; 24(9):2341-7. doi: 10.1093/humrep/dep186. Epub 2009 May 12)

Endometrioses is not only widespread and chronic but is very often incurable. Accordingly, this disease is considered to be a social disease that is life-altering and affects the relationship with society.

Surgery, preferably laparoscopy, has been regarded as the treatment of first intent. Despite this, relapses are very frequent, being around 50% four to five years after surgery.

Since endometrial tissue requires estrogens for its growth and proliferation, a state of hypoestrogenism results in atrophy and regression of endometriosis. This follows from observations of natural or surgical menopause in women as well as in experimental animals. Thus, another possible treatment for endometriosis is hormone therapy blocking the effect of estradiol or its production. Possible treatments in this respect are the contraceptive pill, progestins, or GnRH agonists.

However, inflicting severe hypoestrogenemia over a protracted interval not only causes patients to endure the discomfort of central estrogen deficiency symptoms, such as vasomotor symptoms, vaginal dryness, emotional instability, and insomniam but risks accelerating bone density loss and enhancement of cardiovascular risk factors which are associated with protracted estrogen deprivation. Concerns about the long-term effect in this respect, particularly loss of bone mineral density; have accordingly limited the duration of treatment with GnRH angonist therapy to 6 months for most gynecologic disorders (Surrey E S, Voigt B, Fournet N, Judd H L. *Prolonged gonadotropin-releasing hormone agonist treatment of symptomatic endometriosis: the role of cyclic sodium etidronate and low-dose norethindrone "add-back" therapy*. Fertility and sterility. 1995; 63(4):747-755. Epub 1995 Apr. 1).

Thus, administration of GnRH agonists is affected not only by a large number of undesirable side effects, but also by a high percentage of relapses after the treatments have been suspended.

These adverse effects, especially the observed reductions in bone mineral density when a state of hypoestrogenism is induced by hormone treatment, led to the concept of "add-back" therapy, i.e. small amounts of estrogen or selected progestins was administered concurrently with an GnRH-agonist for reducing the adverse symptoms and the risk of induced bone disease (Barbieri, R. L., *Hormone Treatment of Endometriosis: The Estrogen Threshold Hypothesis*, Am. J. Obstet. Gynecol. 166: 740-5 (1992)).

The rationale for this approach derives from the estrogen threshold hypothesis, which stipulates that estrogen within a certain concentration range may partially prevent bone loss while not stimulating growth of endometrial lesions. The estrogen dependency of endometriosis led Barbieri to propose the hypothesis that concentrations of estradiol over 50 pg/mL were needed to support the growth of endometrial lesions. (Barbieri 1992)

Specifically, the estrogen threshold hypothesis postulates that a therapeutic window of serum estradiol concentration, between 30 and 50 pg/mL, would protect against bone mineral loss and prevent stimulation of endometrial tissue growth. However, it is understood that this therapeutic window can only be obtained using the "add-back" therapy, i.e. by administering small amounts of e.g. estrogen concurrently with the GnRH-agonist However, the "add-back" therapy although effective for reducing some of the systemic adverse effects of the GnRH-agonist therapy, is associated with additional disadvantages. As an example can be mentioned that breakthrough bleeding was reported in up to 40 percent of patients receiving conjugated equine estrogen (Eldred et al., A Randomized, Double-Blind, Placebo-Controlled Trial of the Effects on Bone Metabolism of the Combination of Nafarelin Acetate and Norethisterone, Clin. Endocrinol. (Oxford), 37: 354-9 (1992)).

Furthermore, the administration of the add-back therapy, i.e. an additional drug comprising e.g. estrogen, for controlling the adverse effects of the GnRH-agonist treatment, will compound the disruption which even a single drug might create in the normal physiological activity of a patient. In addition, if a patient forgets to administer one of said drugs, the desired delivery profile of the compound drugs will be lost, possible leading to further adverse effects. Thus, administering more than one drug for therapy, not only adds to the costs but also provide a more complicated dosage regime.

Presently there does not exist a simple and safe medical regimen for treating estrogen related diseases, such as endometriosis, while preventing or reducing the likelihood of developing estrogen deficiency related adverse effects. Accordingly, many women with endometriosis choose repeated surgeries and often struggle to resist addiction to narcotic analgesics because of disabling pain.

Thus, there exists a need for a safe, prophylactic method of affording patients continuing relief of pain for years without having to face the adverse effect of hypoestrogenemia, such as a decrease in bone mineral density.

SUMMARY OF THE INVENTION

Thus, it is a first aspect of the present invention to provide a composition for treating estrogen related diseases, such as endometriosis, while preventing or reducing the likelihood of developing estrogen deficiency related adverse effects.

It is a second aspect of the present invention to provide a composition for treating an estrogen related disease without relying on "add-back" therapy.

It is a third aspect of the present invention to provide a composition for treating an estrogen related disease with a simple dosage regime.

It is a fourth aspect of the present invention to provide a composition for treating an estrogen related disease that increase patient acceptance and compliance of therapy.

These and further aspect are achieved according to the present invention by providing a pharmaceutical composition for treatment of an estrogen related disease while preventing or reducing the likelihood of developing estrogen deficiency related side effects. Said pharmaceutical composition comprises a therapeutically effective amount of at least one GnRH antagonist in the form of a microcrystalline aqueous suspension, and wherein said therapeutically effective amount is sufficient for providing a mean endogenous serum estradiol level of between about 20 pg/ml and 60 pg/ml, preferably between 30 pg/ml and 50 pg/ml, in a patient in a treatment period of at least four weeks, and wherein an "add-back" therapy is not administered to the patient during said treatment period.

Within the context of the present invention the term "add-back therapy" means that small amounts of estrogen or selected progestins is administered concurrently with an GnRH-antagonist for reducing the adverse symptoms of hypoestrogenism e.g. the risk of induced bone disease.

GnRH antagonists are synthetic peptides that compete with the endogenous neurohormone GnRH (also known as luteinizing hormone releasing hormone, LHRH) for binding to its receptors in the anterior pituitary gland. By decreasing or blocking GnRH action, GnRH antagonists suppress release from the anterior pituitary gland of follicle stimulating hormone (FSH) and luteinizing hormone (LH). Thus, GnRH antagonists will block the synthesis of estradiol by the ovaries, creating a state of hypoestrogenism in the patient.

Even though both antagonists and agonists may bind to the GnRH receptors in the pituitary gland, the antagonist will however, immediately block the receptor whereas the agonist operates by first stimulating the receptor, and then "exhausting" the receptor to stop hormone secretion. Thus, use of a GnRH-antagonist provides a preferred immediate onset of action.

The mean endogenous serum estradiol level between about 20 pg/ml and 60 pg/ml, preferably between 30 pg/ml and 50 pg/ml, is preferably maintained for a treatment period of at least four weeks, preferably eight weeks or longer, and can in a preferred embodiment be provided by administrating a single dosage of a GnRH antagonist during the treatment period of at least four weeks. Thus, by using the composition according to the invention, it is possible by administering only one dosage of GnRH antagonist to maintain a desired endogenous serum estradiol level for a treatment period of at least four weeks.

The GnRH antagonist is preferably N-Ac-d-Nal$^1$,d-pCl-Phe$^2$,d-Pal$^3$,d-(Hci)$^6$,Lys(iPr)$^8$,d-Ala$^{10}$ trifluoroacetate (Teverelix TFA), or is selected from the group consisting of Azaline B, Abarelix, Antide, Cetrorelix acetate, and Ganirelix The single dosage of GnRH antagonist may preferably comprise Teverelix TFA in an amount of between 25 and 80 mg, preferably between 30 and 60 mg, and even more preferred around 45 mg. It should in this respect be noted, that a woman's body mass does not influence GnRH activity and thus ovulatory function. This means that the single dosage of GnRH antagonist, e.g. 45 mg Teverelix TFA, is considered to be universal for all women irrespectively of the woman's weight.

The invention also provides a method of treating one or more estrogen related diseases while preventing or reducing the likelihood of developing estrogen deficiency related side effects, wherein said method comprises administering a single dosage of between 25 and 80 mg, preferably between 30 and 60 mg, and even more preferred around 45 mg of the GnRH antagonist Teverelix TFA to a patient in need of said treatment thereby initiating a treatment period of at least four weeks (in which the patient is not administered any additional GnRH antagonist), and wherein a mean endogenous serum estradiol level of between about 20 pg/ml and 60 pg/ml, preferably between about 30 pg/ml and 50 pg/ml, is obtained in said patient during the treatment period, without relying on "add-back" therapy.

A number of estrogen-related disease can be treated using the composition or method according to the invention. However, it is preferred that said estrogen-related disease is endometriosis, but other relevant disease are uterine fibroids, uterine leiomyoma, endometrial cancer, uterine cancer, uterine leiomyosarcomas, ovarian cancer or breast cancer, polycystic ovary syndrome, dysfunctional uterine bleeding, vaginal bleeding, menorrhagia, premenstrual syndrome, migraine headache, cervical intraepithelial neoplasia, adenomyosis and Alzheimer's disease.

BRIEF DESCRIPTION OF THE DRAWING FIGURES

DETAILED DESCRIPTION OF THE INVENTION

Figure 1:
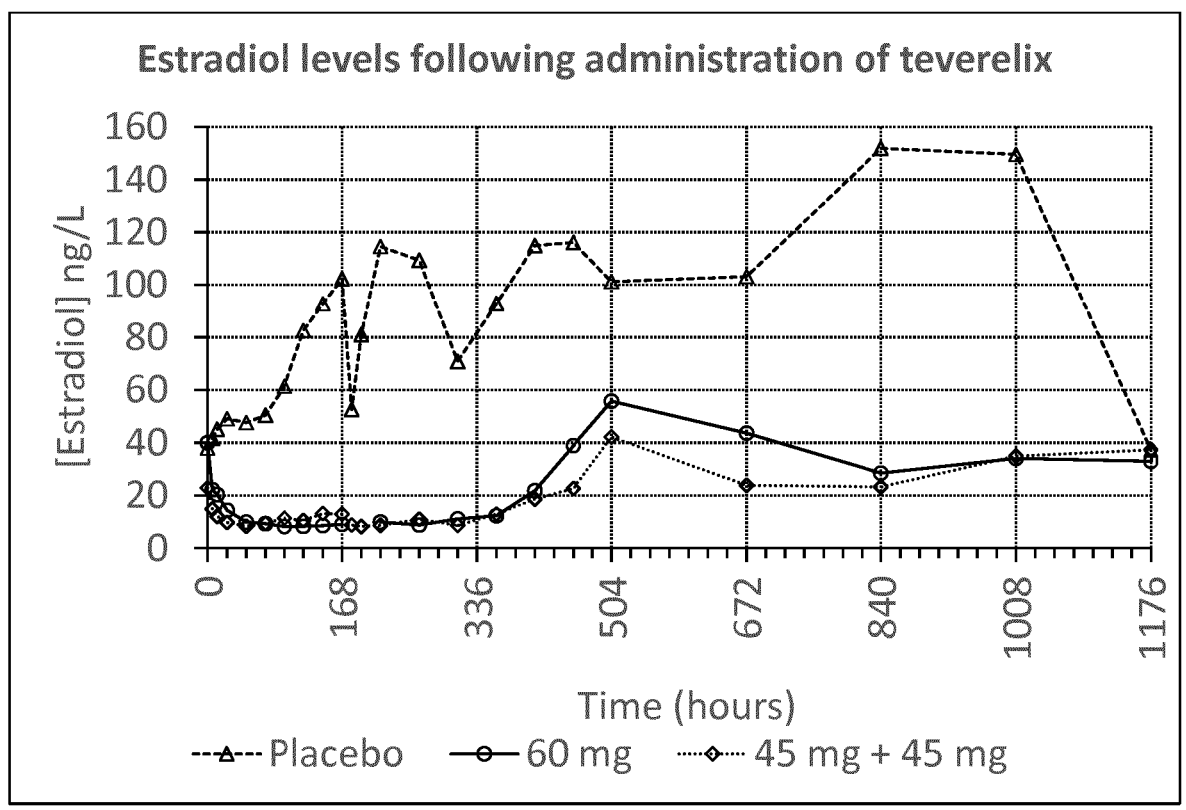
FIG. 1 is a graph showing the mean estradiol concentration in serum of subjects treated with Teverelix TFA, using the composition according to the invention.

The composition for treating the estrogen related disease comprises administering a therapeutically effective amount of a GnRH antagonist to a patient in need of said treatment, said amount of GnRH antagonist is sufficient for providing a mean endogenous serum estradiol level of between about 20 pg/ml and 60 pg/ml, preferably between about 30 pg/ml and 50 pg/ml, in said patient for at least four weeks, without relying on "add-back" therapy.

Even though it is known that lowering the serum estradiol level below 50 pg/ml has the desired effect of inhibiting proliferation of endometrial tissue in a menstruating female, there is a coincident problem of possibly not providing enough estrogen to mitigate, avoid or protect against the menopausal-like symptoms associated with a castrate-like estrogen level. For instance, when the mean endogenous estrogen level falls below about 15 pg/ml, estrogen depletion side-effects occur.

However, in contrast to the treatments known in the art were the side-effects of endogenous estrogen depletion has been prevented by adding back estrogen, i.e. the so "add-back therapy" as suggested by Barberi 1992, the composition of the present invention is capable of not only obtaining a mean endogenous serum estradiol level of between about 30 pg/ml and 50 pg/ml but also maintaining said serum level for at least four weeks without simultaneously administration of small amounts of estrogen.

Thereby is obtained a very effective, simple and inexpensive composition for treating estrogen related diseases. Since, the composition according to the invention does not rely on add-back therapy, the composition will furthermore be more acceptable to patients and more efficient to administer.

An ideal treatment for endometriosis would be a single composition that suppresses estradiol production sufficiently to alleviate the symptoms of endometriosis and other estrogen dependent disorders ideally for a prolonged period of time of at least four weeks, preferable at least eight weeks or even longer, but not to such an extent that serious and irreversible bone loss occurs.

While the amount of GnRH antagonist provided in the regimen of the present invention and the dose may vary in accordance with the particular patient and/or GnRH antagonist, the inventors have found that a single dosage of GnRH antagonist can be sufficient for maintaining a mean endogenous serum estradiol level of between about 30 pg/ml and 50 pg/ml in the patient for a treatment period of at least four weeks, preferably at least eight weeks or even longer, such as up to twelve weeks.

In a preferred embodiment according to the invention the GnRH antagonist is N-Ac-d-Nal$^1$,d-pCl-Phe$^2$,d-Pal$^3$,d-(Hci)$^6$,Lys(iPr)$^8$,d-Ala$^{10}$ trifluoroacetate (Teverelix TFA), however other GnRH antagonist, such as Azaline B, Abarelix, Antide, Cetrorelix acetate, and Ganirelix are also contemplated within the scope of the present invention.

The GnRH antagonist is administered in a microcrystalline aqueous suspension, i.e. in a sustained release formulation, thereby allowing a more uniform and optimal plasma drug profile, and a smoother therapeutic response over the dosage interval. Clinically, this offers the potential to optimise drug therapy and decrease the occurrence of concentration-related adverse effects, reduce the exposure to drug and reduce the cost of drug therapy. In addition, sustained release formulations may increase patient acceptance and compliance of therapy.

In a preferred embodiment the microcrystalline aqueous suspension is preferably one or more of the suspensions disclosed in WO 2003/022243. Said document discloses a method in which the GnRH antagonist, (which is a hydrophobic peptide) is contacted with a counter-ion in an amount and at a molar ratio sufficient to provide a fluid, milky microcrystalline aqueous suspension of the GnRH antagonist without formation of a gel. The specific ratios etc. in order to prepare the suspensions are disclosed in details in WO 2003/022243 (the disclosures of which are hereby incorporated by reference) and will not be discussed in further details in this application.

The inventors have found that such a microcrystalline aqueous suspension, is advantageously in maintaining the mean endogenous serum estradiol level of between about 30 pg/ml and 50 pg/ml in a patient for a prolonged period of time of at least four week and even longer, i.e. for at least eight weeks, without relying on "add-back" therapy, thereby not only allowing regression of endometriotic lesions but also substantially limit the side-effects of hypoestrogenemia.

Thus, a patient in need of treatment only needs to administer a single dosage of GnRH antagonist, e.g. 45 mg Teverelix TFA, every four weeks (i.e. about once a month) or in an even more preferred embodiment a single dosage every eight weeks, (i.e. once every other month).

The single dosage of GnRH antagonist preferably comprises an amount of Teverelix TFA between 25 and 60 mg, preferably between 30 and 45 mg. Dosages above this level has not been shown to be associated with further suppression of the patient's serum estradiol level.

Since body mass does not influence GnRH activity and thus ovulatory function, the single dosage of GnRH antagonist is considered to be universal for all women. The exact dosage of the GnRH antagonist in the formulation will among others depend on the GnRH antagonist used, and/or if more than one GnRH antagonist is present in the composition.

Since the composition according to the present invention ensures that a patients mean endogenous serum estradiol level is maintained between about 20 pg/ml and 60 pg/ml, preferably between about 30 pg/ml and 50 pg/ml, for at least four weeks without simultaneously administration of small amounts of estrogen, said composition provides a superior treatment method compared to the known GnRH antagonist treatments. Not only is a very simple dosage regime provided but the treatment need not be limited to the six months period, which is the standard for the known GnRH antagonist treatments. Accordingly, the present invention provides a composition for effectively treating estrogen related diseases and at the same prevents the risk of relapse.

It will be understood that the composition of the present invention can be used for treating all kinds of estrogen related diseases, and is not limited to endometriosis. Said disease could also be selected from one or more of uterine fibroids, uterine leiomyomas, endometrial cancer, uterine cancer, uterine leiomyosarcomas, ovarian cancer, breast cancer, polycystic ovary syndrome, dysfunctional uterine bleeding, vaginal bleeding, menorrhagia, premenstrual syndrome, migraine headache, cervical intraepithelial neoplasia, adenomyosis and Alzheimer's disease.

Accordingly, the composition according to the present invention allows for a practical administration wherein estrogen levels are low enough to achieve therapeutic benefits from reduced estrogen supplies, but high enough to minimize or avoid the consequences of long-term estrogen deprivation, especially loss of bone mineral density.

EXAMPLES

A number of examples were conducted in order to substantiate that patients can obtain a mean endogenous serum estradiol level of between about 30 pg/ml and 50 pg/ml in a treatment period of at least four weeks, without relying on "add-back" therapy.

Example 1

The Teverelix TFA formulations were manufactured as followed. 0.8 ml or 0.6 ml 5% mannitol were added to the relevant dosage of 60 or 45 mg of the LHRH antagonist Teverelix® trifluoroacetate, respectively. The mixture was stirred using vortex during one minute providing two dosage formulations of Teverelix TFA in a flowing milky pearly microcrystalline aqueous suspensions. The suspensions are made of microcrystals of about 10 μm length. Corresponding placebo formulations, without Teverelix TFA was also prepared Formulation A: 60 mg Teverelix TFA in 0.8 ml 5% mannitol
Formulation B: 45 mg Teverelix TFA in 0.6 ml 5% mannitol
Formulation A placebo: 0.8 ml 5% mannitol
Formulation B placebo: 0.6 ml 5% mannitol A phase I clinical trial with formulation A and B (and placebo) was conducted in order to evaluate the pharmacokinetics, pharmacodynamics, safety and tolerability of Teverelix TFA.

The formulations were each injected subcutaneous (s.c.) as follows:
- A single dosage of formulation A (60 mg Teverelix TFA) administered s.c. on day 3±1 of the menstrual cycle, to 8 healthy female subjects
- A single dosage of formulation A placebo was administered s.c. to on day 3±1 of the menstrual cycle, to 4 healthy female subjects
- Two dosages of formulation B (45 mg Teverelix TFA) administered s.c. to 8 healthy female subjects. The first dosage on day 3±1 of the menstrual cycle and a second dosage administered on day 10±1 of the menstrual cycle, and
- two dosages of formulation B placebo was administered s.c. to 4 healthy female subjects. The first dosage on day 3±1 of the 25 menstrual cycle and a second dosage administered on day 10±1 of the menstrual cycle.

The mean estradiol concentration in the respective subjects was measured. The results are shown in table 1 and 2, respectively and is depicted in FIG. 1 in relation to the placebo data.

TABLE 1

Formulation A - 60 MG TEVERELIX TFA (N = 8)

| Timepoint | Mean (ng/L) | Median (ng/L) | SD (ng/L) | Min (ng/L) | Max (ng/L) | N |
|---|---|---|---|---|---|---|
| PREDOSE | 39.98 | 36.69 | 22.87 | 12.88 | 76.26 | 8 |
| 6 H p.f.a. | 22.18 | 19.75 | 10.76 | 9.03 | 39.35 | 8 |
| 12 H p.f.a. | 20.27 | 16.67 | 13.23 | 9.57 | 50.15 | 8 |
| 24 H p.f.a. | 14.36 | 12.22 | 7.26 | 8.14 | 29.66 | 8 |
| 48 H p.f.a. | 9.86 | 7.99 | 4.93 | 5.66 | 19.71 | 8 |
| 72 H p.f.a. | 9.30 | 9.97 | 3.66 | 4.25 | 15.65 | 8 |
| 96 H p.f.a. | 8.20 | 8.76 | 2.65 | 4.00 | 12.50 | 8 |
| 120 H p.f.a. | 8.33 | 8.20 | 2.30 | 4.25 | 12.26 | 8 |
| 144 H p.f.a. | 8.60 | 7.39 | 3.21 | 5.67 | 15.74 | 8 |
| 168 H p.f.a. | 9.08 | 7.94 | 3.72 | 5.55 | 15.57 | 8 |
| 216 H p.f.a. | 9.88 | 7.73 | 4.87 | 6.40 | 20.02 | 8 |
| 264 H p.f.a. | 8.76 | 7.71 | 3.77 | 3.74 | 14.90 | 8 |
| 312 H p.f.a. | 11.09 | 8.44 | 8.38 | 4.84 | 29.78 | 8 |

TABLE 1-continued

Formulation A - 60 MG TEVERELIX TFA (N = 8)

| Timepoint | Mean (ng/L) | Median (ng/L) | SD (ng/L) | Min (ng/L) | Max (ng/L) | N |
|---|---|---|---|---|---|---|
| 360 H p.f.a. | 12.29 | 9.80 | 11.22 | 4.75 | 38.92 | 8 |
| 408 H p.f.a. | 21.76 | 9.01 | 36.14 | 4.07 | 110.42 | 8 |
| 456 H p.f.a. | 38.94 | 9.32 | 84.43 | 3.27 | 247.63 | 8 |
| 504 H p.f.a. | 55.78 | 9.26 | 129.03 | 4.06 | 374.76 | 8 |
| 672 H p.f.a. | 43.63 | 11.22 | 61.51 | 6.30 | 184.91 | 8 |
| 840 H p.f.a. | 28.49 | 17.09 | 25.25 | 10.87 | 76.27 | 8 |
| 1008 H p.f.a. | 34.09 | 19.60 | 30.97 | 13.90 | 93.94 | 6 |
| 1176 H p.f.a. | 32.93 | 36.46 | 19.42 | 11.38 | 60.71 | 5 |

TABLE 2

Formulation B - 2 × 45 MG TEVERELIX TFA (N = 8)

| Timepoint | Mean (ng/L) | Median (ng/L) | SD (ng/L) | Min (ng/L) | Max (ng/L) | N |
|---|---|---|---|---|---|---|
| PREDOSE | 22.88 | 21.08 | 8.44 | 11.54 | 38.40 | 8 |
| 6 H p.f.a. | 14.85 | 14.11 | 3.83 | 8.37 | 19.94 | 8 |
| 12 H p.f.a. | 12.08 | 11.47 | 2.99 | 8.42 | 17.07 | 8 |
| 24 H p.f.a. | 9.83 | 9.90 | 1.97 | 7.45 | 13.19 | 8 |
| 48 H p.f.a. | 8.32 | 8.73 | 2.24 | 5.26 | 11.35 | 8 |
| 72 H p.f.a. | 9.44 | 9.01 | 3.87 | 5.27 | 14.44 | 8 |
| 96 H p.f.a. | 11.41 | 12.50 | 6.34 | 4.92 | 23.81 | 8 |
| 120 H p.f.a. | 10.50 | 10.83 | 4.71 | 3.58 | 17.57 | 8 |
| 144 H p.f.a. | 13.12 | 14.09 | 6.00 | 3.10 | 21.21 | 8 |
| 168 H p.f.a. | 12.91 | 12.10 | 6.49 | 3.51 | 22.12 | 8 |
| 180 H p.f.a. | 8.84 | 8.83 | 4.00 | 3.69 | 16.10 | 8 |
| 192 H p.f.a. | 8.25 | 7.78 | 4.28 | 4.34 | 17.30 | 8 |
| 216 H p.f.a. | 8.74 | 7.46 | 5.71 | 4.12 | 22.00 | 8 |
| 264 H p.f.a. | 11.01 | 7.94 | 9.33 | 4.56 | 32.92 | 8 |
| 312 H p.f.a. | 8.69 | 7.76 | 4.12 | 4.01 | 14.02 | 8 |
| 360 H p.f.a. | 12.93 | 8.17 | 14.50 | 3.52 | 47.16 | 8 |
| 408 H p.f.a. | 18.58 | 7.72 | 25.59 | 3.77 | 78.47 | 8 |
| 456 H p.f.a. | 22.63 | 7.40 | 41.97 | 3.59 | 125.98 | 8 |
| 504 H p.f.a. | 42.11 | 8.25 | 90.09 | 3.04 | 264.18 | 8 |
| 672 H p.f.a. | 23.85 | 9.13 | 30.82 | 3.23 | 90.19 | 8 |
| 840 H p.f.a. | 23.25 | 15.38 | 25.74 | 3.51 | 79.57 | 8 |
| 1008 H p.f.a. | 34.84 | 15.43 | 43.08 | 4.06 | 130.66 | 8 |
| 1176 H p.f.a. | 37.35 | 15.62 | 39.41 | 4.00 | 109.82 | 7 |

As can be seen in FIG. 1 both doses of Teverelix TFA significantly reduced estradiol concentrations when compared to placebo but yet maintained low levels of estradiol production.

Furthermore, total systemic exposure was approximately 1.5-fold greater following two injections of 45 mg Teverelix TFA administered one week apart compared with a single 60 mg injection, see table 3. Based on these results, a single injection of Teverelix TFA is preferred.

TABLE 3

Total systemic exposure

| Treatment | n | Geometric Mean (CV %) | | | | |
|---|---|---|---|---|---|---|
| | | $Cmax_{Init1}$ (fmol/mL) | $Cmax_{Init2}$ (fmol/mL) | $Cmax_{Late}$ (fmol/mL) | AUC(0-t) (fmol.h/mL) | AUC(0-cq) (fmol.h/mL) |
| 60 mg Teverelix (Treatment Group 1) N = 8 | 8 | 10900 (29.3) | N/A | 2630 (28.8) | 1907000 (39.5) | 1592000 (27.1) |
| 2 × 45 mg Teverelix (Treatment Group 2) N = 8 | 8 | 6030 (22.3) | 7030 (25.3) | 3630 (17.8) | 2833000 (28.8) | 2323000 (18.9) |

Figure 2A:
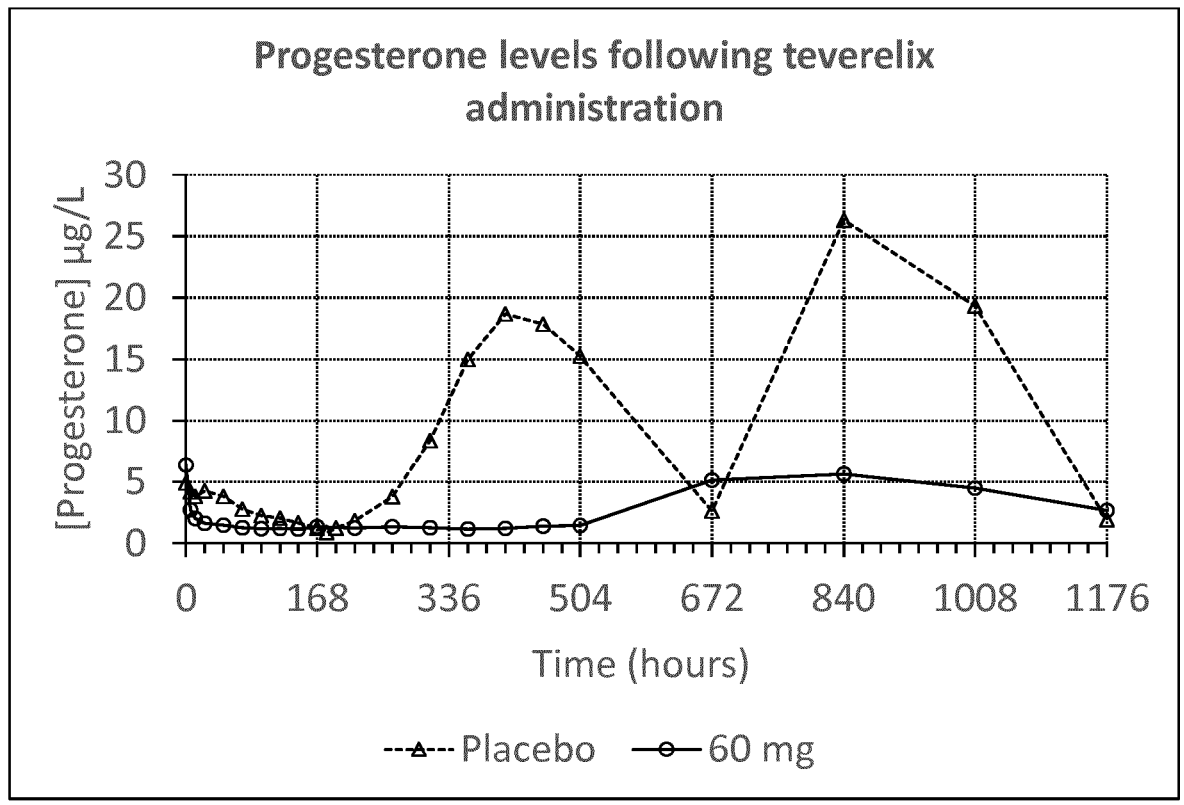
FIG. 2A is a graph showing the mean progesterone values in serum of subjects treated with Teverelix TFA (60 mg), using the composition according to the invention.
Figure 2B:
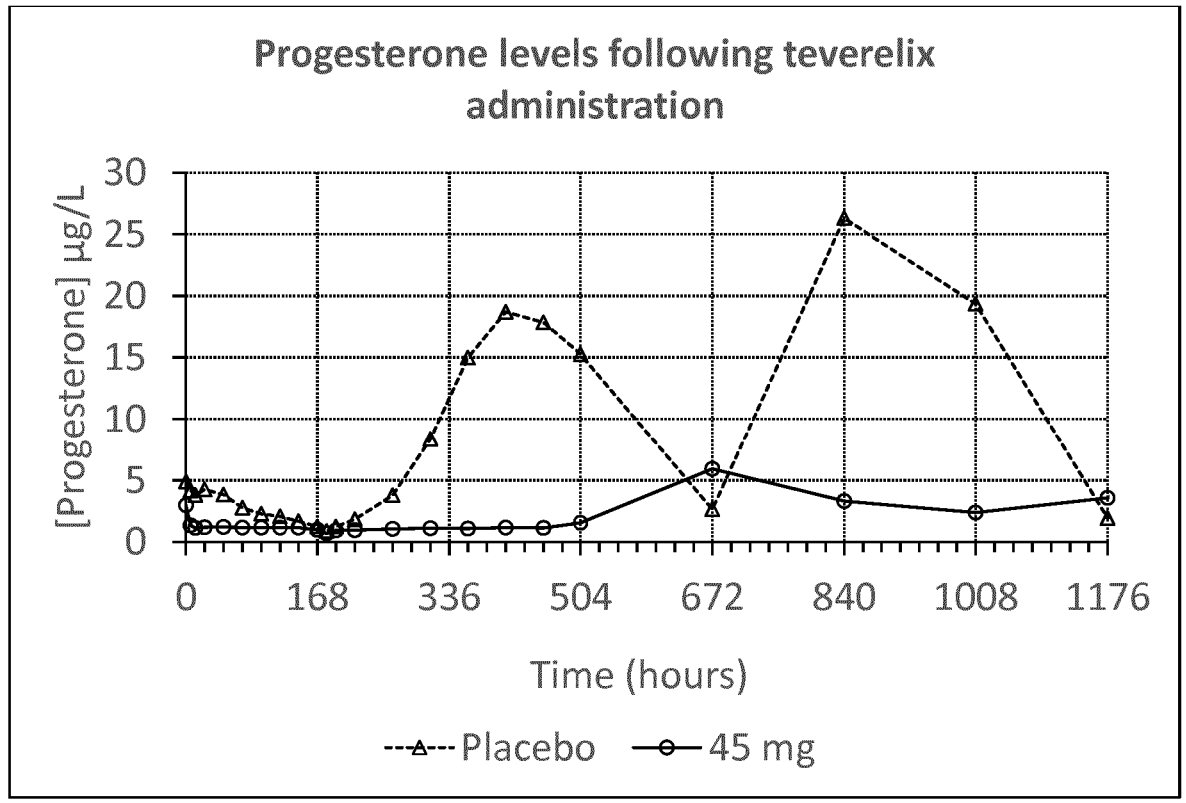
FIG. 2B is a graph showing the mean progesterone values in serum of subjects treated with Teverelix TFA (45 mg), using the composition according to the invention.
Figure 3A:
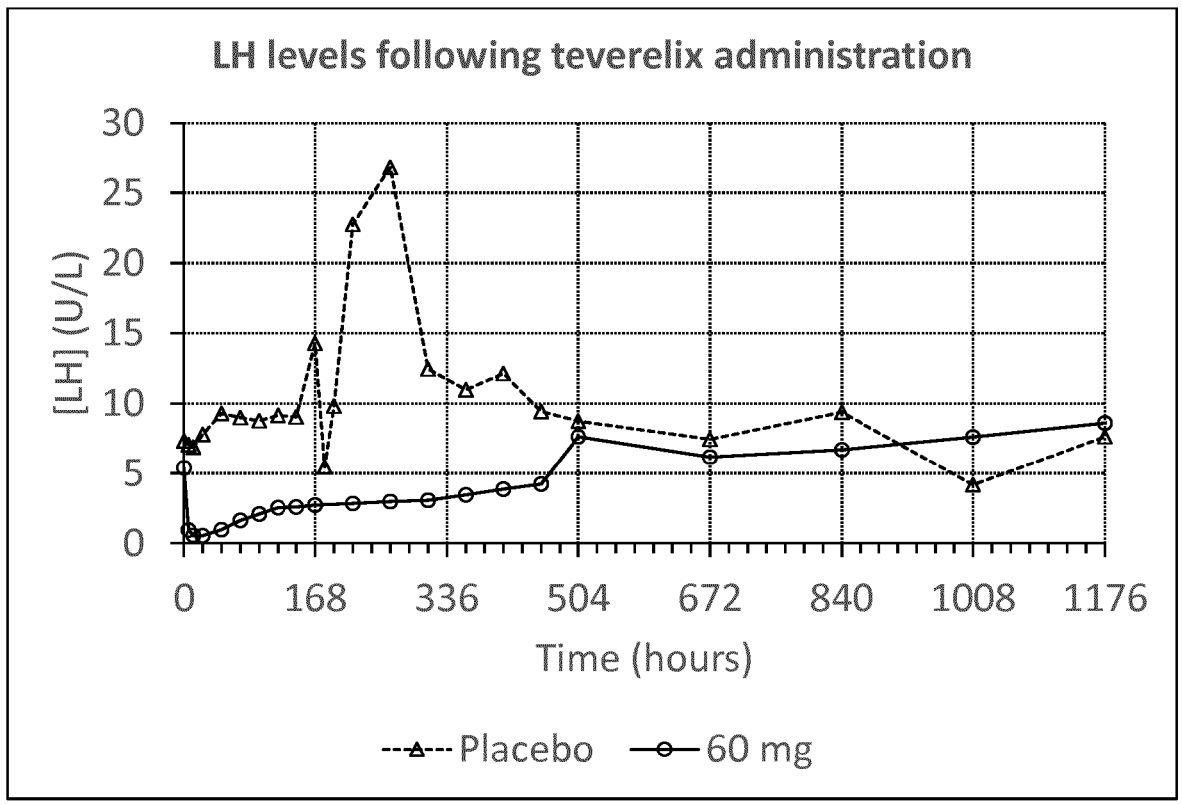
FIG. 3A is a graph showing the mean Luteinizing hormone values in serum of subjects treated with Teverelix TFA (60 mg), using the composition according to the invention.
Figure 3B:
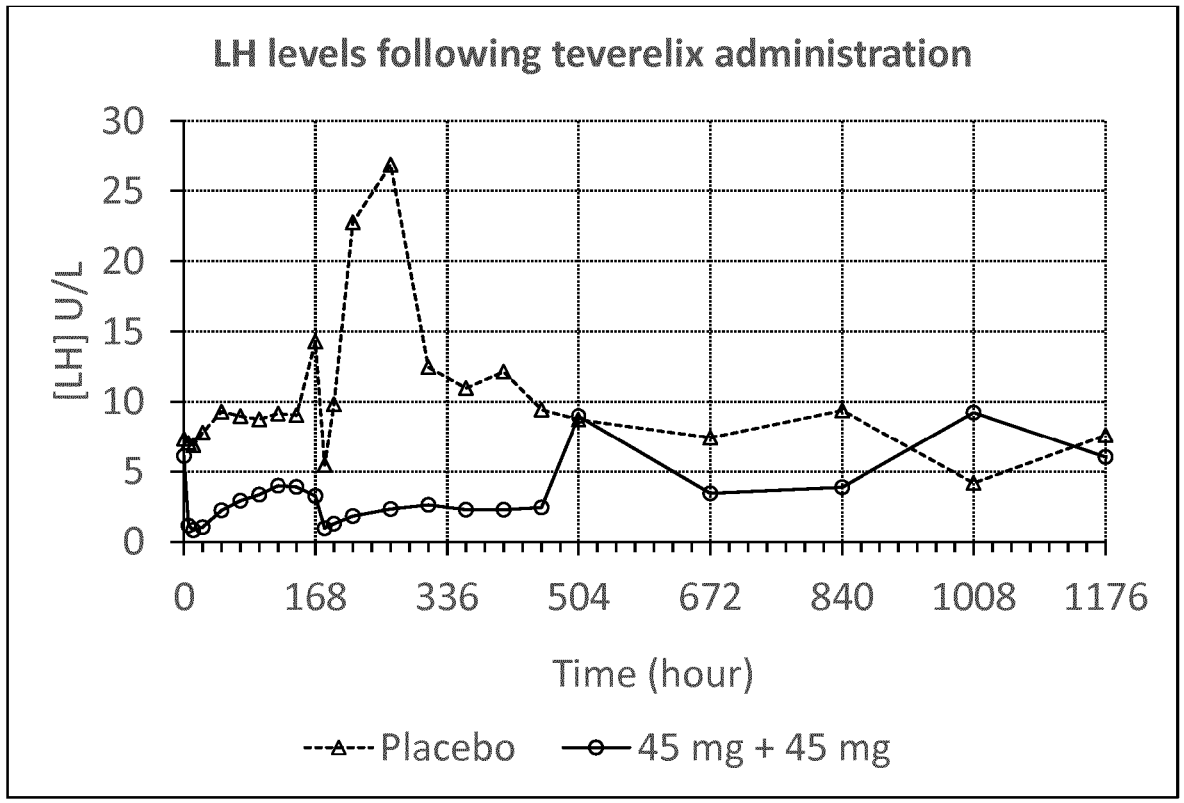
FIG. 3B is a graph showing the mean Luteinizing hormone values in serum of subjects treated with Teverelix TFA (45 mg+45 mg), using the composition according to the invention.
Figure 4A:
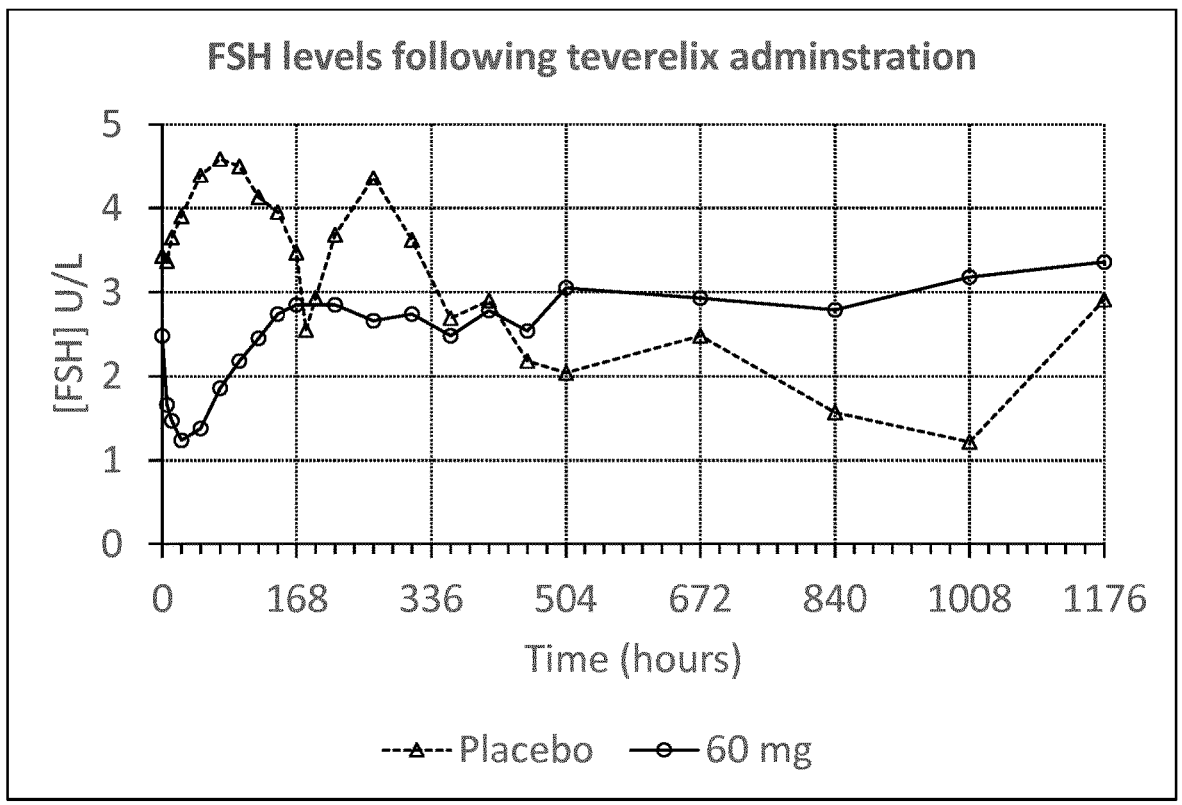
FIG. 4A is a graph showing the mean follicle stimulating Hormone values in serum of subjects treated with Teverelix TFA (60 mg), using the composition according to the invention.
Figure 4B:
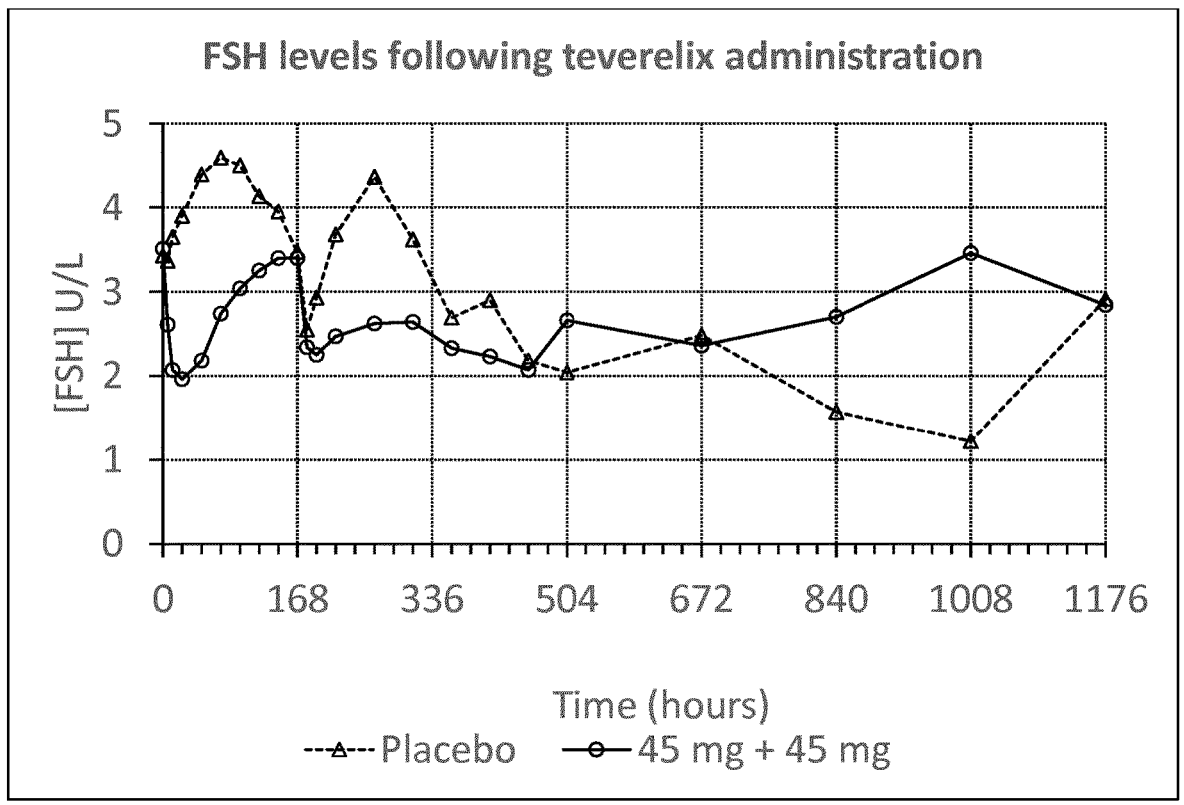
FIG. 4B is a graph showing the mean follicle stimulating Hormone values in serum of subjects treated with Teverelix TFA (45 mg+45 mg), using the composition according to the invention.

Not only did the estradiol concentration decreased after administration of Teverelix TFA, also the concentrations of progesterone, LH and FSH decreased following dosing with Teverelix TFA, see FIGS. 2, 3 and 4. As Teverelix concentrations decreased, hormone levels gradually increased and returned to near baseline when menses reoccurred and sampling ceased.

As is evident from FIG. 1, the mean estradiol concentrations decreased following a single injection of 60 mg Teverelix TFA and remained suppressed until 264 h Post First Administration (p.f.a) where the mean (SD) concentration was −31.22 (23.11) ng/L below baseline. Thereafter, estradiol concentrations began to rise, but remained consistently below baseline until 456 h p.f.a where the mean (SD) concentration was −1.04 (90.98) ng/L below baseline, after which they continued to rise until they returned to near baseline and menses reoccurred in at least one subject at 840 h p.f.a.

A similar trend was apparent following two injections of 45 mg Teverelix TFA administered one week apart. Following the first 45 mg Teverelix TFA injection, estradiol concentrations decreased and remained suppressed until 48 h p.f.a. where the mean (SD) concentration was −14.56 (9.95) ng/L below baseline.

Concentrations then began to rise but remained below baseline until the second injection was administered at 168 h p.f.a. After the second 45 mg Teverelix TFA injection, estradiol concentrations decreased and remained suppressed until 312 h p.f.a. Where the mean (±SD) concentration was −14.20 (10.85) ng/L below baseline. Thereafter, estradiol concentrations began to rise until they returned to near baseline and menses reoccurred in at least one subject at 1008 h p.f.a.

Example 2

A second randomized, single blind, single-center phase I study was conducted.

Two formulations comprising either 45 mg or 30 mg Teverelix TFA and a placebo formulations, were prepared as described in example 1, i.e. the following formulations were prepared
Formulation B: 45 mg Teverelix TFA in 0.8 ml 5% mannitol
Formulation C: 30 mg Teverelix TFA in 0.4 ml 5% mannitol
Formulation B placebo: 0.8 ml 5% mannitol
Formulation C placebo: 0.4 ml 5% mannitol The respective formulations were each injected subcutaneous (s.c.) to 24 subjects—12 per group i.e. 8 on active drug 4 on placebo per group. All subjects received a dose on either the active or placebo s.c. on day 3±1 of the menstrual cycle, i.e.

A single dosage of formulation B (45 mg Teverelix TFA) administered s.c. on day 3±1 of the menstrual cycle, A single dosages of formulation C (30 mg Teverelix TFA) administered s.c. on day 3±1 of the menstrual cycle, and A single dosage of formulation B placebo or formulation C placebo administered s.c. on day 3±1 of the menstrual cycle.

The concentration of Teverelix TFA, and Estradiol was measured over a period of 63 days. Additionally, the effect on Teverelix TFA on two bone markers was measured.

Teverelix TFA Concentrations in Serum

The mean Teverelix TFA concentration in the serum of the respective subjects was measured.

Figure 5:
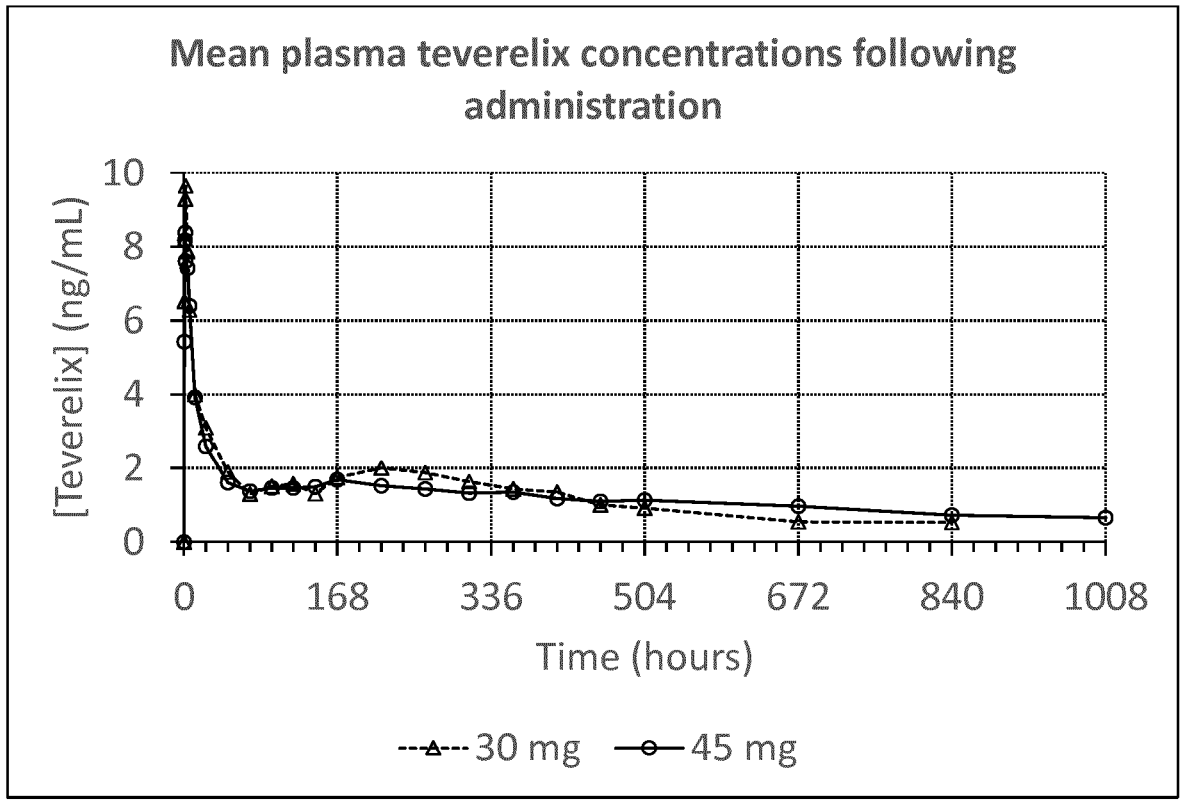
FIG. 5 is a graph showing the mean Teverelix TFA in serum of subjects treated with Teverelix TFA, using the composition according to the invention.

The results are shown in table 4 and FIG. 5, showing that the Teverelix TFA reached peak concentration within 1.5 and 2 hours then gradually declined over a 48-hour period. However, quantifiable levels were seen with the 45 mg dose for the entire 64-day measurement period and for 42 days with the 30 mg dose.

TABLE 4

Mean Teverelix TFA concentrations

| Time (h) | Mean (ng/L) Placebo | Mean (ng/L) 30 mg | Mean (ng/L) 45 mg | Mean (ng/L) 30 + 45 mg |
|---|---|---|---|---|
| 0 | 0.00 | 0.00 | 0.00 | 0.00 |
| 0.5 | 0.00 | 6.52 | 5.43 | 5.79 |
| 1 | 0.00 | 8.20 | 8.17 | 8.18 |
| 1.5 | 0.00 | 9.29 | 8.38 | 8.73 |
| 2 | 0.00 | 9.64 | 7.61 | 8.39 |
| 4 | 0.00 | 7.86 | 7.42 | 7.59 |
| 6 | 0.00 | 6.28 | 6.40 | 6.36 |
| 12 | 0.00 | 4.00 | 3.92 | 3.95 |
| 24 | 0.00 | 3.10 | 2.60 | 2.79 |
| 48 | 0.00 | 1.89 | 1.61 | 1.70 |
| 72 | 0.00 | 1.29 | 1.38 | 1.35 |
| 96 | 0.00 | 1.50 | 1.46 | 1.48 |
| 120 | 0.00 | 1.57 | 1.46 | 1.49 |
| 144 | 0.00 | 1.30 | 1.50 | 1.42 |
| 168 | 0.00 | 1.74 | 1.69 | 1.70 |
| 216 | 0.00 | 2.00 | 1.52 | 1.68 |
| 264 | 0.00 | 1.87 | 1.43 | 1.58 |
| 312 | 0.00 | 1.64 | 1.32 | 1.43 |
| 360 | 0.00 | 1.44 | 1.34 | 1.37 |
| 408 | 0.00 | 1.35 | 1.18 | 1.23 |
| 456 | 0.00 | 1.02 | 1.09 | 1.06 |
| 504 | 0.00 | 0.95 | 1.13 | 1.07 |
| 672 | 0.00 | 0.71 | 0.97 | 0.85 |

TABLE 4-continued

Mean Teverelix TFA concentrations

| Time (h) | Mean (ng/L) Placebo | Mean (ng/L) 30 mg | Mean (ng/L) 45 mg | Mean (ng/L) 30 + 45 mg |
|---|---|---|---|---|
| 840 | 0.00 | 0.60 | 0.72 | 0.67 |
| 1008 | 0.00 | n.a. | 0.84 | 0.84 |
| 1176 | 0.00 | n.a. | 0.77 | 0.77 |
| 1344 | 0.00 | n.a. | 0.70 | 0.70 |
| 1512 | 0.00 | n.a. | 0.57 | 0.57 |

Estradiol Concentrations in Serum

The mean estradiol concentration in the respective subjects was measured as described in example 1.

Figure 6:
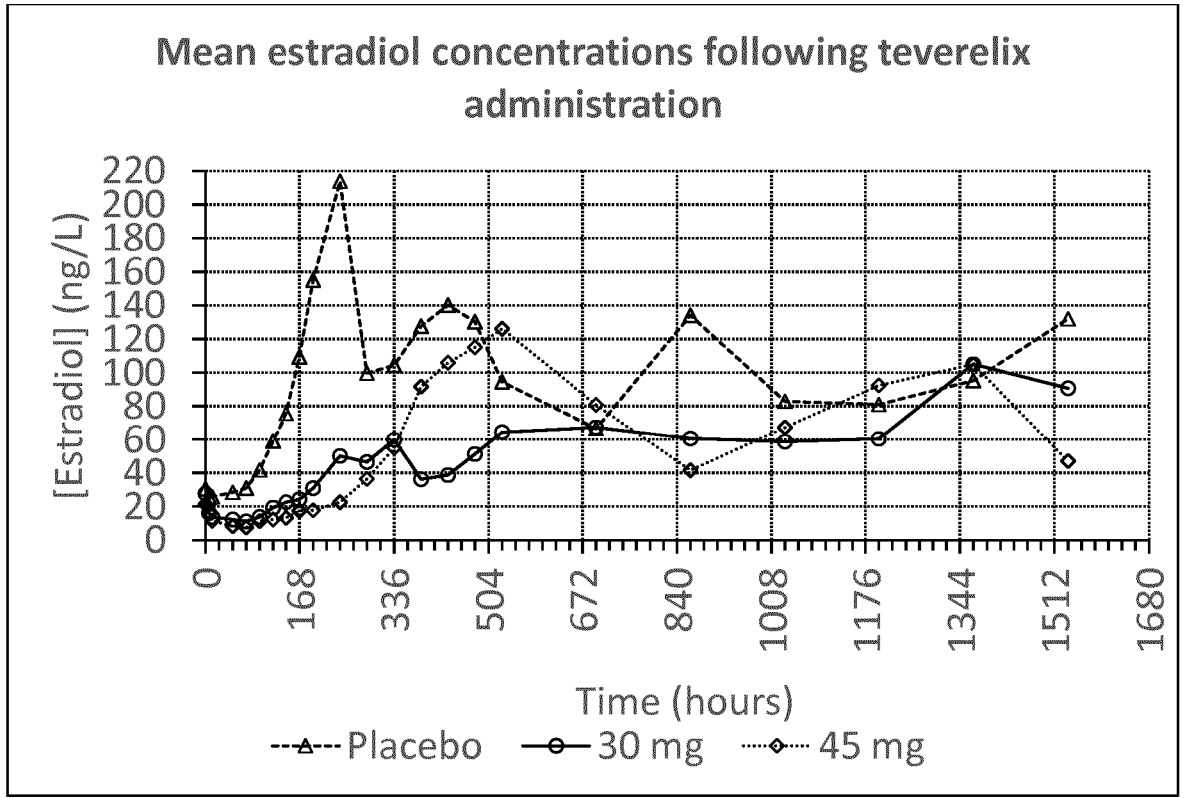
FIG. 6 is a graph showing the mean estradiol concentration in serum of subjects treated with Teverelix TFA, using the composition according to the invention.

The results are shown in table 5 and FIG. 6, showing that women in the 30 mg group had mean baseline estradiol levels of 27.7 ng/L; this was reduced to a nadir of 11.2 ng/L on day 2.

TABLE 5

Mean Estradiol concentrations

| Time (days) | Mean (ng/L) Placebo | Mean (ng/L) 30 mg dosage | Mean (ng/L) 45 mg dosage | Mean (ng/L) 30 + 45 mg |
|---|---|---|---|---|
| 0 | 30.6 | 27.7 | 21.5 | 24.6 |
| 0.25 | 25.5 | 16.1 | 16.3 | 16.2 |
| 0.5 | 25.8 | 13.8 | 11.5 | 12.7 |
| 1 | 28.5 | 12.3 | 8.4 | 10.4 |
| 2 | 31.0 | 11.2 | 7.5 | 9.4 |
| 3 | 41.8 | 13.7 | 11.4 | 12.6 |
| 4 | 59.2 | 19.4 | 12.3 | 15.8 |
| 5 | 75.6 | 22.6 | 13.3 | 17.9 |
| 6 | 109.3 | 24.4 | 17.5 | 20.9 |
| 7 | 155.0 | 31.0 | 17.8 | 24.4 |
| 9 | 213.8 | 50.2 | 22.6 | 36.4 |
| 11 | 99.7 | 46.5 | 36.4 | 41.8 |
| 13 | 104.5 | 59.9 | 54.9 | 57.2 |
| 15 | 127.6 | 36.3 | 91.6 | 64.0 |
| 17 | 140.2 | 38.7 | 105.9 | 72.3 |
| 19 | 130.4 | 51.4 | 115.1 | 83.3 |
| 21 | 94.6 | 64.5 | 126.1 | 95.3 |
| 28 | 66.5 | 67.4 | 80.9 | 74.1 |
| 35 | 135.1 | 60.7 | 41.6 | 51.1 |
| 42 | 82.9 | 58.6 | 67.4 | 63.0 |
| 49 | 81.1 | 60.5. | 92.4 | 76.4 |
| 56 | 95.3 | 105.1 | 104.9 | 105.0 |
| 63 | 132.1 | 90.7 | 47.1 | 68.9 |

Women in the 45 mg group had mean estradiol baseline levels of 21.5 ng/L and this was reduced to a nadir of 7.5 ng/L on day 2. Estradiol levels returned to baseline by day 8 in the 30 mg group and day 9 in the 45 mg group. All women in the placebo group had estradiol peaks consistent with ovulations during the study period (64 days).

Based on peak estradiol levels it appears that only one of the 8 women in the 30 mg and 5 of the 8 women in the 45 mg group ovulated during the study period. This observation is highly correlated with peak LH data. In only two of the 24 women did there appear to be a discrepancy between a lack of peak estradiol levels and an LH surge. Progesterone measurements were generally consistent with the above.

As is evident from FIG. 6 estradiol levels can be maintained during a prolonged period, albeit at low levels. A mean of 40.5 pg/mL was found for the 30 mg dose and a mean of 49.0 pg/mL for the 45 mg dose when a GnRH antagonist, Teverelix TFA, was administered every two months.

Thus, the mean concentrations of estradiol using the composition according to the present invention is below 50 pg/mL, i.e. below the estradiol concentrations which according to the estrogen threshold hypothesis are needed to support the growth of endometrial lesions, and high enough to minimize or avoid the consequences of long-term estrogen deprivation, especially loss of bone mineral density, (Barbieri 1992).

As is evident from this example said preferred concentration regime of estradiol was maintained for about 60 days, i.e. about four weeks without relying on add-back therapy.

CTX and DPD Concentrations.

In order to evaluate the effect of the treatment with Teverelix TFA on the bone mineral density, two biochemical bone mineral markers was measured in the subjects. Telopeptides type I collagen, cross-linked, N-terminal (CTX) was measured in serum of the treated subjects, and deoxypyridinoline (DPD) was measured in the subject's urine.

Said bone markers were measured on the following days in the test period: 1 (pre-dose), 15, 29, 43, 57, 64

DPD is a dynamic biochemical marker of bone loss. An increase in DPD levels in an early morning urine specimen is a reliable indicator of increased bone loss. The CTX test measures for the presence and concentration of a crosslink peptide sequence of type I collagen, found, among other tissues, in bone. This specific peptide sequence relates to bone turnover because it is the portion that is cleaved by osteoclasts during bone resorption, and its serum levels are therefore proportional to osteoclastic activity at the time the blood sample is drawn.

Figure 7:
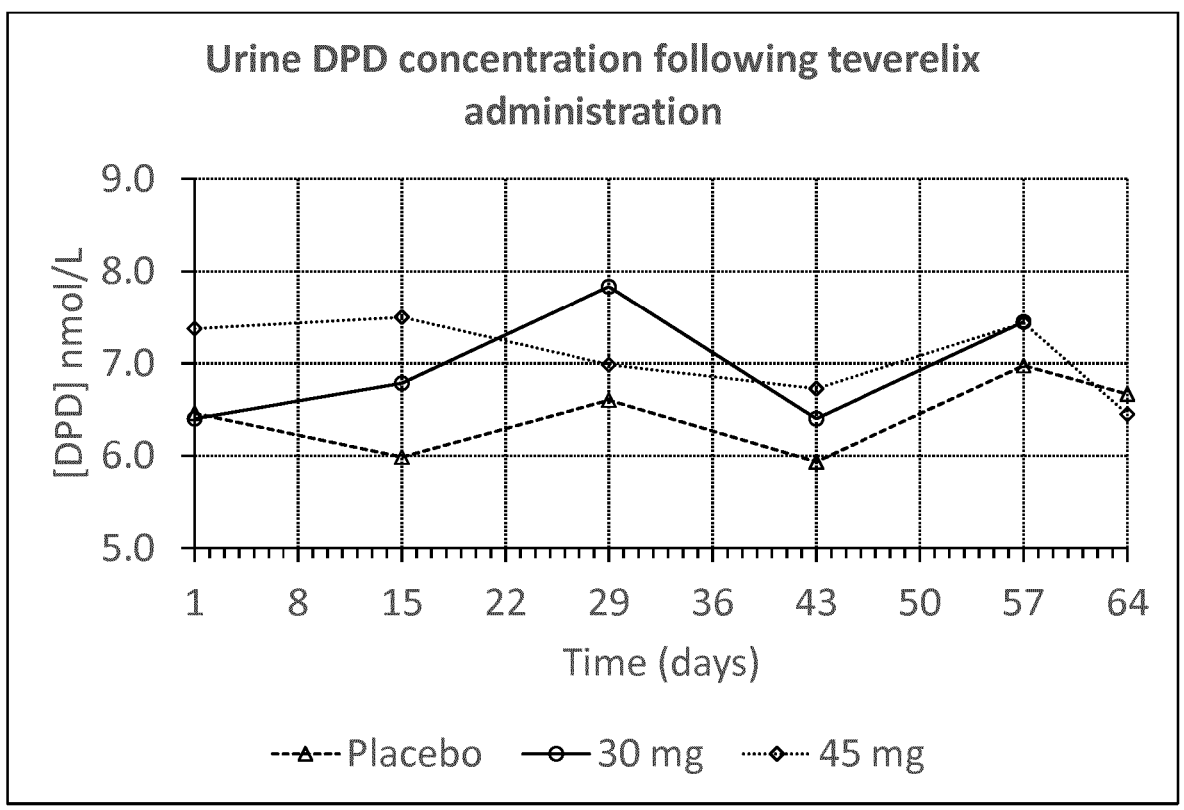
FIG. 7 is a graph showing the mean deoxypyridinoline concentration in urine of subjects treated with Teverelix TFA, using the composition according to the invention.

The concentration of DPD and CTX test were carried out at MOS Pharma Services, Central Lab GmbH, Grossmoorbogen 25, 21079 Hamburg, Germany by means of highly sensitive and specific validated chemi-luminescent (CUA) and enzyme-linked immuno-sorbent (ELISA) methods. The results are shown in FIG. 7 and table 6 respectively.

TABLE 6

CTX data

| Day | Mean (ng/L) Placebo | Mean (ng/L) 30 mg | Mean (ng/L) 45 mg |
|---|---|---|---|
| 1 | 19.6 | 16.7 | 22.6 |
| 15 | 19.6 | 17.1 | 22.4 |
| 29 | 20 | 17 | 21.6 |
| 43 | 18.7 | 16.7 | 22 |
| 57 | 17 | 16.5 | 19.3 |
| 64 | 18.2 | 16.2 | 17.3 |

As is evident from table 6, and FIG. 7, no significant alteration in the bone markers, urine DPD and serum CTX, was observed during the course of the study, confirming that the therapeutic window of serum estradiol concentration, between 30 and 50 pg/mL, protected against a reduction in bone mineral density.

In accordance with the present invention, a regimen or dose of GnRH antagonist is provided which is effective to inhibit proliferation of endometrial tissue in a menstruating female but is ineffective to substantially stop production of endogenous estrogen.

The formulations used in the present invention is inexpensive to manufacture, and due to the ease of use it provides a very simple dosage regime.

Modifications and combinations of the above principles and combinations are foreseen within the scope of the present invention.

The invention claimed is:

1. A pharmaceutical composition for the treatment of an endometriosis while preventing or reducing the likelihood of developing bone loss, said composition comprises a therapeutically effective amount of at least one Gonadotrophin-releasing hormone (GnRH) antagonist administered in a sustained release formulation in the form of a microcrystalline aqueous suspension, wherein said therapeutically effective amount is sufficient for providing a mean endogenous serum estradiol level of between about 20 pg/ml and 60 pg/ml, in a patient in a treatment period of at least four weeks, over the treatment period, wherein an add-back therapy is not administered to the patient during the treatment period, wherein the mean endogenous serum estradiol level is provided by a single dosage of a therapeutically effective amount of GnRH antagonist, wherein the GnRH antagonist is N-Ac-d-Nal$^1$,d-pCl-Phe$^2$,d-Pal$^3$,d-(Hci)$^6$,Lys (iPr)$^8$,d-Ala$^{10}$ trifluoro-acetate (Teverelix TFA), and wherein the therapeutically effective amount is between 25 and 80 mg of Teverelix TFA.

2. The composition according to claim 1, wherein the mean endogenous serum estradiol level is between about 30 pg/ml and 50 pg/ml in a patient in a treatment period of at least four weeks.

3. The composition according to claim 1, wherein the mean endogenous serum estradiol level is between 30 pg/ml and 50 pg/ml.

4. A method of treating endometriosis while preventing or reducing the likelihood of developing bone loss, wherein said method comprises administering a single dosage of between 25 and 80 mg of the GnRH antagonist, Teverelix TFA administered in a sustained release formulation in the form of a microcrystalline aqueous suspension, to a patient in need of said treatment thereby initiating a treatment period of at least four weeks, and wherein a mean endogenous serum estradiol level of between about 20 pg/ml and 60 pg/ml is obtained in said patient over the treatment period, without relying on add-back therapy.

* * * * *